United States Patent [19]

Horwell et al.

[11] Patent Number: 4,855,316

[45] Date of Patent: Aug. 8, 1989

[54] 1,2-DIAMINO-4,5-DIMETHOXYCY-CLOHEXYL AMIDE ANALGESIC COMPOUNDS

[75] Inventors: David C. Horwell, Foxton, England; Stephen J. Johnson, Ann Arbor, Mich.

[73] Assignee: Warner-Lambert Company, Morris Plains, N.J.

[21] Appl. No.: 161,563

[22] Filed: Feb. 18, 1988

[51] Int. Cl.[4] .................. A61K 31/40; C07D 295/08; C07D 295/10

[52] U.S. Cl. .................. 514/422; 514/429; 540/450; 540/480; 540/481; 540/596; 546/196; 546/202; 546/203; 546/205; 546/207; 548/525; 548/528; 548/578; 548/950; 549/59; 549/60; 549/76; 549/467; 549/494

[58] Field of Search .................. 548/525, 528, 578; 514/422, 429

[56] References Cited

U.S. PATENT DOCUMENTS

| | | | |
|---|---|---|---|
| 4,598,087 | 7/1986 | Horwell | 514/429 |
| 4,632,935 | 12/1986 | Kaplan | 514/429 |
| 4,656,182 | 4/1987 | Horwell | 514/324 |
| 4,663,343 | 5/1987 | Horwell et al. | 514/429 |
| 4,677,122 | 6/1987 | Horwell | 514/622 |
| 4,737,493 | 4/1988 | Horwell | 514/212 |

*Primary Examiner*—Joseph Paul Brust
*Attorney, Agent, or Firm*—Ronald A. Daignault

[57] ABSTRACT

Certain 1,2-diamino-4,5-dimethoxycyclohexane amide derivatives have analgesic activity, and bind selectively to the kappa opioid receptor site. Pharmaceutical compositions containing these compounds, and a method of alleviating pain in mammals are also disclosed.

16 Claims, No Drawings

1,2-DIAMINO-4,5-DIMETHOXYCYCLOHEXYL AMIDE ANALGESIC COMPOUNDS

BACKGROUND OF THE INVENTION

The present invention relates to compounds having biological activity, to pharmaceutical compositions containing the compounds, and to a medical method of treatment.

More particularly, the present invention concerns certain 1,2diamino-4,5-dimethoxycyclohexane amide derivatives have analgesic activity, to pharmaceutical compositions containing these compounds, and to a method of alleviating pain in mammals by administering the pharmaceutical compositions.

The search for strong analgesics which also possess minimal potential for dependency has been among the highest priority efforts in pharmaceutical research. These research efforts have, to a great extent, involved chemical modification of the opiate structure and the discovery of novel compounds which possess morphine-like activity.

The discovery of endogenous opioids has led workers in the field to consider that these peptides, possessing less rigid structures, might interact with opioid receptors other than those which the classical rigid structure opiates, such as morphine, bind.

The concept of multiple opioid receptors has been supported by studies with nalorphine and a series of benzomorphans which display unusual pharmacological properties dissimilar from morphine, yet blocked by the selective opioid antagonists. [See, for example, W. R. Martin, et al, *J. Pharmacol. Exp. Ther.*, 197: 517–532 (1976).]

The existence of multiple types of opioid receptors is of importance because it suggests the possibility of separating the desirable analgesic and psychotherapeutic effects of a drug compound from the undesirable abuse potential or habituating effects.

U.S. Pat. No. 4,098,904 discloses certain cis- and trans-N-(2-aminocycloaliphatic)benzamide compounds having analgesic activity.

U.S. Pat. No. 4,145,435 describes certain 2-aminocycloaliphatic amide compounds as analgesics. In particular, trans-3,4-dichloro-N-[2-pyrrolidinyl)-cyclohexyl]benzacetamide is reported to possess selective kappa agonist activity, and therefor to possess analgesic activity without attendant dependence liability. [See P. V. Vonvoigtlander, et al., *J. Pharmacol. Exp. Ther.*, 224: 7–12 (1983).]

U.S. Pat No. 4,212,878 discloses certain N-[(4-mono- or di-oxygen-group-substituted-1-amino-cyclohex-1-yl)methyl)phenylacetamides, particularly 2-(3,4dichlorophenyl)-N[[8-(1pyrrolidinyl)-1,4-diaxaspiro[4.5]-dec-8-yl]methyl]acetamide having analgesic properties.

U.S. Pat. No. 4,359,476 discloses certain N-[2-amino(oxy or thio group) substituted cycloaliphatic]-phenylacetamide and -benzamide compounds having the oxy- or thio group substituents on a cycloaliphatic ring carbon adjacent to either of the nitrogen-bearing carbon atoms of the cycloaliphatic ring. These compounds, having analgesic activity are typified by cis- and trans-4-bromo-N-[3-methoxy-2-(1-pyrrolidinyl)cyclohexyl]-N-methylbenzamide.

U.S. Pat. No. 4,598,087 and its divisional, U.S. Pat. No. 4,677,122, disclose certain oxy- or thioacetamides of trans-1,2-diaminocyclohexane having analgesic activity. These compounds are typified by trans-2-(2,3-dichlorophenoxy)-N-methyl-N-[2-(1-pyrrolidinyl)cyclohexyl]acetamide.

U.S. Pat. No. 4,656,182 discloses certain trans-N-methyl-N-[2-(1-pyrrolidinyl)cyclohexyl]benzo[b]thiophene acetamides having analgesic activity.

U.S. Pat. No. 4,663,343 discloses certain trans-N-methyl-N-[2-(1-pyrrolidinyl)cyclohexyl]-naphthalenyloxy-and naphthalenylthioacetamides having analgesic activity.

SUMMARY OF THE INVENTION

The present invention provides a class of amides of trans-1,2-diamino-4,5-dimethoxycyclohexanes which possess selective kappa receptor analgesic activity. In its broadest chemical compound aspect, the present invention provides compounds of Formula I

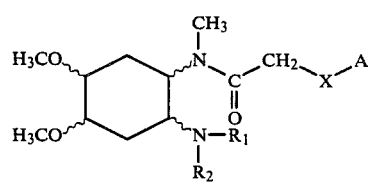

wherein the methoxyl groups are cis to one another and the two nitrogen atoms are trans to one another. X is a direct bond, or is —O— or —S— and $R_1$ is methyl and $R_2$ is selected from hydrogen; alkyl of from one to six carbon atoms;

—$CH_2CH=CR_3R_4$; —$CH_2C\equiv CR_3$; 2- or 3-thienyl; or

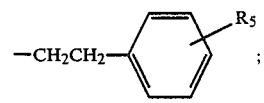

where $R_3$ and $R_4$ are independently hydrogen or methyl; and $R_5$ is selected from hydrogen, flourine, chlorine, bromine, alkyl of from one to four carbon atoms, or alkoxy of from one to four carbon atoms.

Alternatively, $R_1$ and $R_2$, together with the nitrogen atom to which they are attached may form a ring denoted by

where n is an integer of from three to eight.

The substituent group A is selected from

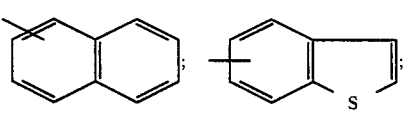

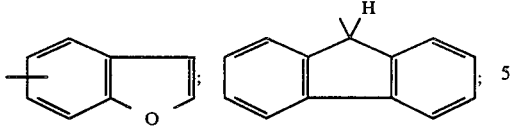

phenyl; phenyl substituted with from one to four halogen atoms; phenyl substituted with one or two alkyl groups of from one to four carbon atoms; phenyl substituted with one or two alkoxy groups of from one to four carbon atoms; or phenyl substituted with one or two alkyl groups of from one to four carbon atoms and one or two halogen atoms.

In a second aspect, the present invention provides pharmaceutical compositions for alleviating pain in a mammal comprising a compound as defined above in combination with a pharmaceutically acceptable carrier.

In a third aspect, the present invention provides a method of alleviating pain in a mammal comprising administering to a mammal in need of such treatment an analgesically effective amount of a compound as defined above.

DETAILED DESCRIPTION

Compounds of the present invention comprise a class of derivatives of trans-1,2-diamino-4,5-dimethoxycyclohexane in which one nitrogen atom of the diamine is substituted with methyl and a second substituent, $R_2$ (as defined above), or preferably is part of a heterocyclic pyrrolidinyl, piperidinyl, or hexahydro-1H-azepinyl ring. The second nitrogen atom of the diamine is a N-methyl amide nitrogen further substituted with the group —X—A wherein X and A are as defined above.

By virtue of the two amine and two methoxy groups attached to the cyclohexane ring, the compounds of the present invention possess at least four asymmetric centers, giving rise to $2_4$ (or 16) possible stereoisomers. Other asymmetric centers may exist depending upon the nature of the substituent A. The compounds of the present invention are limited to the subclass wherein the two nitrogen atoms attached to the cyclohexane ring are trans to one another, thus limiting the possibilities to eight out of the possible 16 stereoisomers. The method of preparing the compounds of the present invention results in compounds in which the two methoxyl substituents are cis to one another, further limiting the compounds of the present invention to a subclass of four out of the possible 16 stereoisomers. The compounds of the present invention thus form a group of compounds defined by the following structural formulae Ia-Id (in which the cyclohexane ring is shown as planar for clarity):

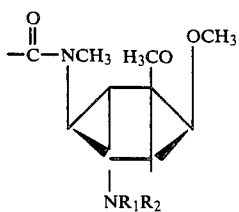

Ia

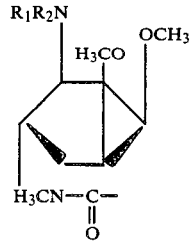

Ib

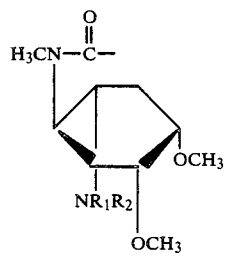

Ic

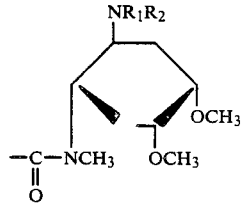

Id

The present invention contemplates all stereoisomers falling within the class defined by structures Ia-Id above as well as mixtures thereof in all possible cyclohexane ring conformations. Individual stereoisomers are obtained, if desired, from mixtures thereof by known methods of resolution.

Specific examples of compounds falling within the scope of this invention include, but are not necessarily limited to:

[1R-(1α,2β,4β, 5β)]-N-[4,5-Dimethoxy-2-(1-pyrrolidinyl)cyclohexyl]-N-methyl-4-benzofuranacetamide.

[1S-(1α,2β,4β,5β)]-N-[4,5-Dimethoxy-2-(1-pyrrolidinyl)cyclohexyl]-N-methyl-4-benzofuranacetamide.

[1R-(1α,2β,4α,5α)]-N-[4,5-Dimethoxy-2-(1-pyrrolidinyl)cyclohexyl]-N-methyl-4-benzofuranacetamide.

[1S-(1α,2β,4α,5α)]-N-[4,5-Dimethoxy-2-(1-pyrrolidinyl)cyclohexyl]-N-methyl-4-benzofuranacetamide.

[1R-(1α,2β,4β,5β)]-N-[4,5-Dimethoxy-2-(1-pyrrolidinyl)cyclohexyl]-N-methylbenzo[b]thiophene-4-acetamide.

[1S-(1α,2β,4β,5β)]-N-[4,5-Dimethoxy-2-(1-pyrrolidinyl)cyclohexyl]-N-methylbenzo[b]thiophene-4-acetamide.

[1R-(1α,2β,4α,5α)]-N-[4,5-Dimethoxy-2-(1-pyrrolidinyl)cyclohexyl]-N-methylbenzo[b]thiophene-4-acetamide.

[1S-(1α,2β,4α,5α)]-N-[4,5-Dimethoxy-2-(1-pyrrolidinyl)cyclohexyl]-N-methylbenzo[b]thiophene-4-acetamide.

[1R-(1α,2β,4β,5β)]-2-(4-Chloro-3,5-dimethylphenoxy)-N-[4,5-dimethoxy-2-(1-pyrrolidinyl)cyclohexyl]-N-methylacetamide.

[1S-(1α,2β,4β,5β)]-2-(4-Chloro-3,5-dimethylphenoxy)-N-[4,5-dimethoxy-2-(1-pyrrolidinyl)cyclohexyl]-N-methylacetamide.

[1R-(1α,2β,4α,5α)]-2-(4-Chloro-3,5-dimethylphenoxy)-N-[4,5-dimethoxy-2-(1-pyrrolidinyl)cyclohexyl]-N-methylacetamide.

[1S-(1α,2β,4α,5α)]-2-(4-Chloro-3,5-dimethylphenoxy)-N-[4,5-dimethoxy-2-(1-pyrrolidinyl)cyclohexyl]-N-methylacetamide.

[1R-(1α,2β,4β,6β)]-N-[4,5-Dimethoxy-2-(1-pyrrolidinyl)cyclohexyl]-N-methyl-1-naphthaleneacetamide.

[1S-(1α,2β,4β,5β)]-N-[4,5-Dimethoxy-2-(1-pyrrolidinyl)cyclohexyl]-N-methyl-1-naphthaleneacetamide.

[1R-(1α,2β,4α,5α)]-N-[4,5-Dimethoxy-2-(1-pyrrolidinyl)cyclohexyl]-N-methyl-1-naphthaleneacetamide.

[1S-(1α,2β,4α,5α)]-N-[4,5-Dimethoxy-2-(1-pyrrolidinyl)cyclohexyl]-N-methyl-1-naphthaleneacetamide.

[1R-(1α,2β,4β,5β)]-2-(3,4-Dichlorophenoxy)-N-[4,5-dimethoxy-2-(1-pyrrolidinyl)cyclohexyl]-N-methylacetamide.

[1S-(1α,2β,4β,5β)]-2-(3,4-Dichlorophenoxy)-N-[4,5-dimethoxy-2-(1-pyrrolidinyl)cyclohexyl]-N-methylacetamide.

[1R-(1α,2β,4α,5α)]-2-(3,4-Dichlorophenoxy)-N-[4,5-dimethoxy-2-(1-pyrrolidinyl)cyclohexyl]-N-methylacetamide.

[1S-(1α,2β,4α,5α)]-2-(3,4-Dichlorophenoxy)-n-[4,5-dimethoxy-2-(1-pyrrolidinyl)cyclohexyl]-N-methylacetamide.

[1R-(1α,2β,4β,5β)]-3,4-Dichloro-N-[4,5-dimethoxy-2-(1-pyrrolidinyl)cyclohexyl]-N-methylbenzeneacetamide.

[1S-(1α,2β,4β,5β)]-3,4-Dichloro-N-[4,5-dimethoxy-2-(1-pyrrolidinyl)cyclohexyl]-N-methylbenzeneacetamide.

[1R-(1α,2β,4α,5α)]-3,4-Dichloro-N-[4,5-dimethoxy-2-(1-pyrrolidinyl)cyclohexyl]-N-methylbenzeneacetamide.

[1S-(1α,2β,4α,5α)]-3,4-Dichloro-N-[4,5-dimethoxy-2-(1-pyrrolidinyl)cyclohexyl]-N-methylbenzeneacetamide.

[1R-(1α,2β,4β,5β)]-N-[4,5-Dimethoxy-2-(1-pyrrolidinyl)cyclohexyl]-2-(3-fluorophenoxy)-N-methylacetamide.

[1S-(1α,2β,4β,5β)]-N-[4,5-Dimethoxy-2-(1-pyrrolidinyl)cyclohexyl]-2-(3-fluorophenoxy)-N-methylacetamide.

[1R-(1α,2β,4α,5α)]-N-[4,5-Dimethoxy-2-(1-pyrrolidinyl)cyclohexyl]-2-(3-fluorophenoxy)-N-methylacetamide.

[1S-(1α,2β,4α,5α)]-N-[4,5-Dimethoxy-2-(1-pyrrolidinyl)cyclohexyl]-2-(3-fluorophenoxy)-N-methylacetamide.

[1R-(1α,2β,4β,5β)]-2-(2,4-Dichloro-3,5-dimethylphenoxy)-N-[4,5-dimethoxy-2-(1-pyrrolidinyl)cyclohexyl]-N-methylacetamide.

[1S-(1α,2β,4β,5β)]-2-(2,4-Dichloro-3,5-dimethylphenoxy)-N-[4,5-dimethoxy-2-(1-pyrrolidinyl)cyclohexyl]-N-methylacetamide.

[1R-(1α,2β,4α,5α)]-2-(2,4-Dichloro-3,5-dimethylphenoxy)-N-[4,5-dimethoxy-2-(1-pyrrolidinyl)cyclohexyl]-N-methylacetamide.

[1S-(1α,2β,4α,5α)]-2-(2,4-Dichloro-3,5-dimethylphenoxy)-N-[4,5-dimethoxy-2-(1-pyrrolidinyl)cyclohexyl]-N-methylacetamide.

[1R-(1α,2β,4β,5β)]-N-[4,5-Dimethoxy-2-(1-pyrrolidinyl)cyclohexyl]-N-methyl-9H-fluorene-9-carboxamide.

[1S-(1α,2β,4β,5β)]-N-[4,5-Dimethoxy-2-(1-pyrrolidinyl)cyclohexyl]-N-methyl-9H-fluorene-9-carboxamide.

[1R-(1α,2β,4α,5α)]-N-[4,5-Dimethoxy-2-(1-pyrrolidinyl)cyclohexyl]-N-methyl-9H-fluorene-9-carboxamide.

[1S-(1α,2β,4α,5α)]-N-[4,5-Dimethoxy-2-(1-pyrrolidinyl)cyclohexyl]-N-methyl-9H-fluorene-9-carboxamide.

[1R-(1α,2β,4β,5β)]-N-[4,5-Dimethoxy-2-(1-pyrrolidinyl)cyclohexyl]-N-methyl-2-(2,3,4,5-tetrachlorophenoxy)acetamide.

[1S-(1α,2β,4β,5β)]-N-[4,5-Dimethoxy-2-(1-pyrrolidinyl)cyclohexyl]-N-methyl-2-(2,3,4,5-tetrachlorophenoxy)acetamide.

[1R-(1α,2β,4α,5α)]-N-[4,5-Dimethoxy-2-(1-pyrrolidinyl)cyclohexyl]-N-methyl-2-(2,3,4,5-tetrachlorophenoxy)acetamide.

[1S-(1α,2β,4α,5α)]-N-[4,5-Dimethoxy-2-(1-pyrrolidinyl)cyclohexyl]-N-methyl-2-(2,3,4,5-tetrachlorophenoxy)acetamide.

The compounds of the present invention are prepared by a series of chemical steps detailed in the following Reaction Sequence.

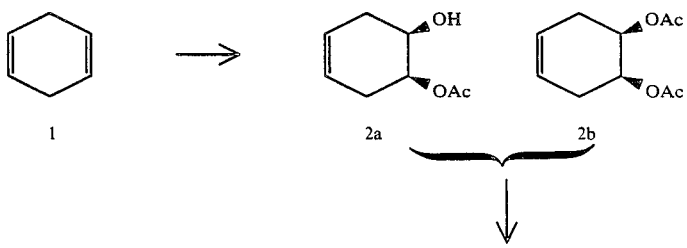

Reaction Sequence

Reaction Sequence

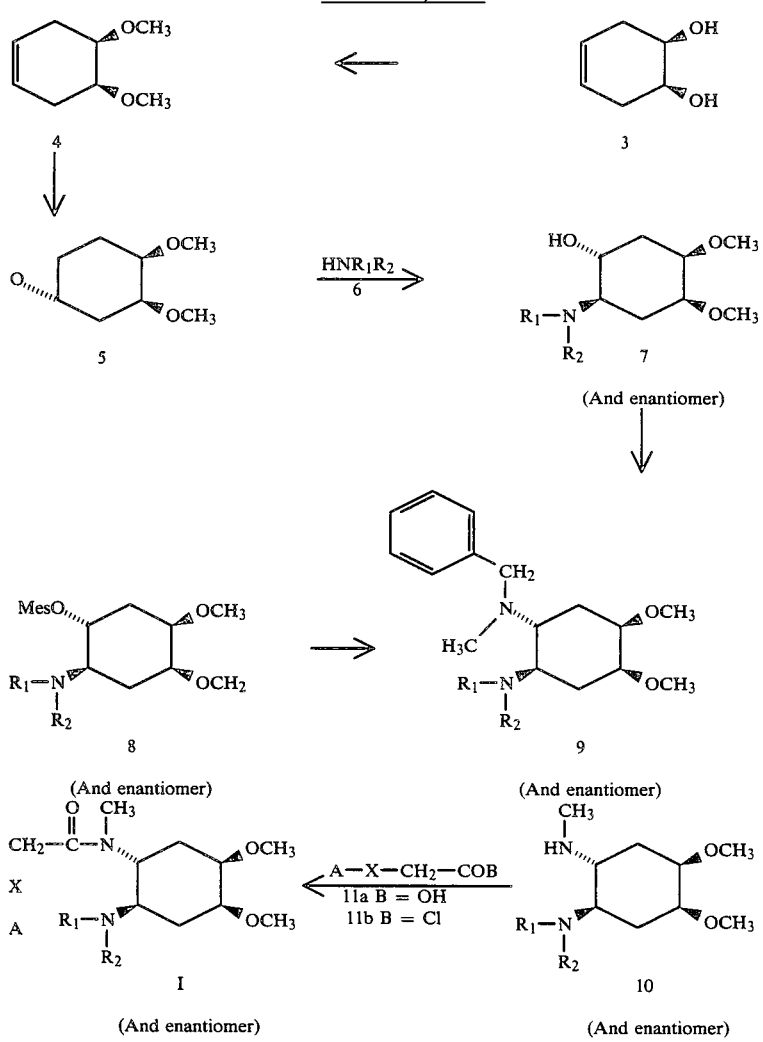

1,4-Cyclohexadiene, 1, is oxidized in glacial acetic acid/sodium acetate by the action of a mixture of iodine and sodium iodate to produce a mixture of the acetoxyhydroxy cyclohexene, 2a, and the diacetoxycyclohexene, 2b. This mixture of hydroxyester and diester compounds is treated with potassium hydroxide in diethyl ether to produce the cis-4,5-dihydroxycyclohexene, 3.

The cis4,5-dihydroxycyclohexene, 3, is treated with sodium hydride in dry ether or tetrahydrofuran, followed by methyl iodide, to prepare the cis-4,5-dimethoxycyclohexene, 4.

The cis-4,5-dimethoxycyclohexene, 4, is next epoxidized by the action of m-chloroperbenzoic acid in dichloromethane to yield the dimethoxycyclohexane epoxide, 5. Reaction of 5 with the desired amine, 6, results in the 1-hydroxy-2-(substituted)amino-4,5-dimethoxycyclohexane compound, 7.

Compound 7 is next converted to the mesylate (methanesulfonate ester, 8) by reaction with methanesulfonyl chloride in dichloromethane in the presence of an acid scavenger such as triethylamine. As shown in the Reaction Sequence, one pair of enantiomers of 10 is produced by reacting epoxide 5 with $R_1R_2NH$, followed by reaction of the mesylate, 8, formed therefrom with benzylmethylamine, and subsequent hydrogenolysis over palladium on carbon. The other enantiomeric pair, in which the two amine groups of compound 10 are reversed, is produced by a similar sequence of steps, but involving reaction of epoxide 5 first with benzylmethylamine followed by $R_1R_2NH$.

The compounds of the present invention are finally produced by reacting the appropriately-substituted acetic acid, 11a, or acid chloride, 11b, or the corresponding oxy- or thioacetic acids or acid chlorides with the amine, 10.

The various acetic acids, oxyacetic acids, or thioacetic acids used to prepare the intermediate acid chlorides are generally known or, if not previously known, are readily prepared by methods generally known to the art.

By virtue of the basic nitrogen on the cyclohexane moiety, pharmaceutically acceptable salts of compounds of the present invention may be prepared by reaction with appropriate acids. Suitable acids for the formation of pharmaceutically acceptable salts of the compounds of this invention form a class well known to practitioners of the pharmaceutical formulation arts (cf. S. M. Berge, et al, "Pharmaceutical Salts" in *J. Pharm. Sci.*, 66: 1–19 (1977)), and include such acids as hydrochloric, hydrobromic, hydriodic, sulfuric, nitric, phosphoric, acetic, benzoic, citric, maleic, tartaric, succinic, gluconic, ascorbic, sulphamic, oxalic, pamoic, methanesulfonic, benzenesulfonic, ethanesulfonic, hydroxyethanesulfonic, and related acids and mixtures thereof.

The salts are generally prepared by reacting the free base with one equivalent of the desired acid in the appropriate unreactive solvent, followed by collection of the salt by filtration or recovery upon removal of the solvent. The free base may be regenerated, if desired, by reaction of the salt with one equivalent of a base such as sodium hydroxide, sodium bicarbonate, sodium carbonate and the like. The salts may differ from the free base form of compounds of this invention in properties such as melting point and solubility in polar solvents, but are otherwise considered equivalent for the purpose of this invention.

The compounds of the present invention possess significant analgesic activity with the potential for minimum dependence liability due to their selective kappa opioid receptor binding properties. In addition to producing analgesia, compounds which are selective kappa antagonists, such as the compounds of this invention, also cause opioid receptor-mediated sedation, diuresis, and corticosteroid elevation. Accordingly, the compounds of this invention may also be useful as diuretics and psychoterapeutic agents as well as analgesics.

Representative compounds of the present invention demonstrate positive activity in standard laboratory analgesic tests in animals such as mice. The $ED_{50}$ doses for several representative compounds of this invention in the standard rat paw pressure analgesia test are presented in Table 1.

Representative compounds of the present invention, were also tested in vitro to determine the extent of opioid receptor binding, and were found to selectively bind to the kappa opioid receptor site with evidence of little or no binding to the mu or delta opioid receptors. The benefits of this selectivity in binding has been discussed above and is also described by M. B. Tyers, *Br. J. Pharm.*, (1980) 69: 503–512.

TABLE 1

| Compound | R₁ R₂ | X | A | Rat Paw Pressure MPE₅₀ (mg.kg i.v.) |
|---|---|---|---|---|
| 1 | Pyrrolidinyl | Bond | 4-Benzo[b]furanyl | 1.5 |
| 2 | Pyrrolidinyl | Bond | 4-Benzo[b]thiophenyl | 0.8 |
| 3 | Pyrrolidinyl | —O— | 4 >10 dimethyl-phenyl | |
| 4 | Pyrrolidinyl | —O— | 3,4-Dichlorophenyl | >10 |
| 5 | Pyrrolidinyl | Bond | 1-Naphthyl | 1.7 |
| 6 | Pyrrolidinyl | Bond | 3,4-Dichlorophenyl | 5.2 |

Measurement of the kappa opioid binding activity of compounds of this invention was made by the following method. Guinea pig brain homogenates were prepared fresh daily utilizing the method of Gillan, et al, *Br. J. Pharm.*, (1980) 70: 481–490. The binding of tritiated etorphine to brain homogenate tissue was measured in the presence of unlabelled competitor compounds of this invention with 200 nanomolar D-Ala-D-Leu-enkephalin (acronym DADLE) and 200 nanomolar D-Ala-MePheGly-ol-enkephalin (acronym DAGO) added to saturate the delta and mu receptor site, respectively. The reaction was terminated by rapid filtration, and the radioactivity bound to the filters counted by liquid scintillation spectrophotometry.

Measurements of the mu and delta opioid receptor binding of compounds of this invention were made by the following method. Guinea pig brain homogenates were prepared fresh daily employing the method of Gillan, et al cited above.

Homogenates were incubated for 150 minutes at 0° C. with either tritiated DAGO to measure mu receptor site binding activity, or tritiated DADLE in the presence of a tenfold excess of unlabeled DAGO to measure the delta receptor site binding activity. Nonspecific binding was determined in the presence of $10^{-6}$M DAGO and $10^{-6}$ DADLE.

The data was analyzed by the method of Scatchard, *Ann. N.Y. Acad. Sci.*, 51: 660–672 (1949) and Hill, *J. Physiol.*, 40 IV–VIII (1910). The inhibition of binding of tritiated etorphine, DAGO, and DADLE by cold ligands was determined from the regression of log percentage inhibition of specific binding or log concentration of cold ligand. The inhibition constant, $K_i$, was calculated from the equation:

$$K_i = \frac{IC_{50}}{1 + [L] K_D}$$

where [L] is the concentration of the labeled ligand and $K_D$ is the equilibrium dissociation constant.

The results of these tests for several representative compounds of this invention are presented in Table 2.

Compounds of the present invention and/or their nontoxic, pharmaceutically acceptable salts may be administered to mammals orally in combination with convention compatible carriers in solid or in liquid form. These oral pharmaceutical compositions may contain conventional ingredients such as binding agents selected from syrups, acacia, gelatin, sorbitol, tragacanth, polyvinylpyrrolidone, and mixtures thereof. The compositions may further include fillers such as lactose, mannitols, starch, calcium phosphate, sorbitol, methylcellulose and mixtures thereof.

TABLE 2

| | | | | Opoid Binding | |
|---|---|---|---|---|---|
| Compound | R₁ R₂ | X | A | Kappa $K_i$ nm | Mu $K_i$ nm |
| 1 | Pyrrolidinyl | Bond | 4-Benzo[b]furanyl | 18 | 2800 |
| 2 | Pyrrolidinyl | Bond | 4-Benzo[b]16 thiophenyl | 820 | |
| 3 | Pyrrolidinyl | —O— | 4-Chloro-3,5-dimethyl-phenyl | 180 | 720 |
| 4 | Pyrrolidinyl | —O— | 3,4-Dichloro-phenyl | 270 | 1100 |
| 5 | Pyrrolidinyl | Bond | 1-Naphthyl | 39 | 6600 |
| 6 | Pyrrolidinyl | Bond | 3,4-Dichloro- | 23 | 500 |

TABLE 2-continued

[Structure: cyclohexane ring with H3CO, H3CO substituents, N(CH3)-C(=O)-CH2-X-A group, and N(R1)(R2) group, ·HCl, (±)]

| Compound | R₁ R₂ | X | A | Opoid Binding Kappa K_i nm | Mu K_i nm |
|---|---|---|---|---|---|
| 7 | Pyrrolidinyl | Bond | phenyl 9-Fluorenyl | 8.7 | 273 |
| 8 | Pyrrolidinyl | —O— | 2,4-Dichloro-3,5-dimethyl-phenyl | 150 | 700 |
| 9 | Pyrrolidinyl | —O— | 3-Fluoro-phenyl | 400 | 1100 |

These oral compositions may also contain lubricants such as magnesium stearate, high molecular weight polymers such as polyethylene glycol, high molecular weight fatty acids such as stearic acid, silica, or agents to facilitate disintegration of the solid formulation such as starch, and wetting agents such as sodium lauryl sulfate.

The solid oral compositions may take any convenient form such as tablets, lozenges, capsules, or dry powders which may be reconstituted with water or other suitable liquid prior to administration.

Liquid form pharmaceutical compositions may take the form of solutions, suspensions, or emulsions. The liquid forms may contain flavorants, sweeteners, and/or preservatives such as alkyl p-hydroxybenzoates. They may further contain suspending agents such as sorbitol, glucose, or other sugar syrups, methyl-, hydroxymethyl-or carboxymethylcellulose, and gelatin, emulsifying agents such as lecithin or sorbitol monooleate, and conventional thickening agents.

Liquid compositions may optionally be encapsulated in, for example, gelatin capsules in an effective amount.

The compounds of this invention may also be administered to mammals rectally in the form of suppositories. For preparing suppositories, a low-melting wax such as a mixture of fatty acid glycerides or cocoa butter is first melted, and the active ingredient is dispersed homogeneously in the melt. The mixture is then poured into convenient sized molds and allowed to cool and solidify.

Preferably, the pharmaceutical compositions of this invention are in unit dosage form. In such form, the preparation is subdivided into unit doses containing appropriate amounts of the active component. The unit doses can be a packaged preparation with the package containing discrete quantities of the preparation. For example, the package may take the form of packaged tablets, capsules, and powders in envelopes, vials or ampoules, The unit dosage form can also be a capsule, cachet, or tablet itself or can be the appropriate number of any of these in package form.

The quantity of active compound in a unit dose of preparation may be varied or adjusted from about 0.5 mg to about 350 mg according to the particular application and the potency of the active ingredient.

When employed systematically in therapeutic use as analgesic agents in the pharmaceutical method of this invention, the compounds are administered at doses of from about 0.05 mg to about 2.0 mg of active compound per kilogram of the recipient.

GENERAL SYNTHETIC METHODS

In general, the compounds of the present invention are prepared by reacting the appropriate 1,2-diamino-4,5-dimethoxycyclohexane compound with the desired carboxylic acid or a reactive derivative thereof such as the acid chloride or acyl imidazole.

The carboxylic acids may be coupled directly to the amine in the presence of a coupling reagents such as dicyclohexylcarbodiimide or the like. This reaction is generally carried out in a suitable solvent such as tetrahydrofuran or dioxane at ambient temperature but, depending upon the reactivity of the specific starting materials employed, the reaction time, solvent employed, and reaction temperature may be varied. Reaction temperatures of between about −25° C. and the boiling point of the solvent are employed.

The reaction between the acid chlorides and the amine is generally carried out at ambient temperature in a suitable solvent such as chloroform or dichloromethane in the presence of an acid acceptor such as a tertiary amine or alkaline earth metal carbonate or bicarbonate. The mixture of amine and acid halide is allowed to stand until the reaction is essentially complete.

Alternatively the desired starting carboxylic acid may first be converted to the corresponding acyl amidazole compound by conventional methods. The acyl imidazole is then reacted with the amine in the conventional manner to produce the compounds of this invention.

In an alternative method for preparing compounds of this invention where R₁ is methyl and R₂ is an unsaturated group, the desired carboxylic acid (or reactive intermediate thereof) is reacted with N-methyl-1,2-diamino-4,5-dimethoxycyclohexane to form the intermediate amide where R₁ is methyl and R₂ is hydrogen. This intermediate is then further reacted with a reactive alkenyl or alkynyl halide such as allyl chloride or bromide or propargyl chloride or bromide, or the like to form compounds where R₂ is allyl, propargyl, and the like.

The desired product of any of the foregoing methods is recovered from the reaction mixture by techniques well known in the art. Particular enantiomers may be separated by formation of the appropriate salt such as the [D]- or [L]-tartrate salts and resolution of the diastereomers by fractional recrystallization.

The following examples are provided to enable one skilled in the art to practice the present invention, but are not to be read as limiting the scope of the invention as it is defined by the appended claims.

EXAMPLE 1

Preparation of N-[4,5-Dimethoxy-2-(1-pyrrolidinyl)cyclohexyl]-2-(3-fluorophenoxy)-N-methylacetamide

Step 1

Preparation of cis-4,5-Cyclohexenediol

A mixture of 1,4-cyclohexadiene (310 mmol), iodine (156 mmol) and sodium iodate (84 mmol) in 50 mL of glacial acetic acid was stirred at room temperature for 18 hours. Sodium acetate (320 mmol) was added and the resulting mixture heated under reflux for seven hours and then allowed to stand at room temperature overnight. The acetic acid was removed under vacuum to give a dark syrup which was diluted with diethyl ether and washed with sodium bisulfite solution until the iodine had been decolorized. The phases were separated and the aqueous phase extracted with ethyl acetate. The combined organic layers were dried over anhydrous magnesium sulfate and concentrated to yield a yellow syrup.

Thin layer chromatography of this crude reaction mixture (eluting with a 1:1 mixture of hexane and ethyl acetate) showed three spots corresponding to the iodiacetate, the diacetate, and the monoacetate.

This crude mixture of acetates was taken up in ether and 10% potassium hydroxide in methanol was added until chromatographic analysis of the reaction mixture indicated the absence of starting material. The reaction mixture was neutralized by the addition of solid carbon dioxide and the mixture concentrated to a brown syrup. This material was distilled at 100°–110° C. at 1 mm Hg to yield 4,5-cyclohexenediol as a white crystalline solid.

The proton magnetic resonance spectrum (CDCl$_3$) showed peaks at δ 2.1–2.4 (4 protons, multiplet), δ 3.75 (2 protons, broad singlet), δ 3.90 (2 protons, broad singlet), δ 5.55 (2 protons, singlet).

Step 2

Preparation of 4,5-Dimethoxycyclohexene

The diol from Step 1 (0.88 mmol) was dissolved in 10 mL of dry tetrahydrofuran and treated with 5.3 mmol of sodium hydride followed by 4.4 mmol of methyl iodide. This mixture was stirred at room temperature for 50 minutes until thin-layer chromatographic analysis of the reaction mixture showed the absence of starting material.

The reaction was quenched by the addition of moist diethyl ether, and the ether layer was separated, washed with water, and dried over anhydrous magnesium sulfate. The solution was concentrated and the residue distilled to yield 4,5-dimethoxycyclohexene, bp 90°–100° C. at 20 mm Hg.

The proton magnetic resonance spectrum (CDCl$_3$) showed peaks at δ 2.1–2.4 (4 protons, multiplet), δ 3.4 (6 protons, singlet), δ 3.6 (2 protons, multiplet), and δ 5.6 (2 protons, singlet).

Step 3

Preparation of 4,5-dimethoxy-7-oxa-bicyclo[4.1.0]heptane

The 4,5-dimethoxycyclohexene from Step 2 (15.14 mmol) was dissolved in 10 mL of dichloomethane and the resulting solution cooled to 0° C. To this cooled mixture was added in a dropwise manner a solution of 15.15 mmol of m-chloroperbenzoic acid in 30 mL of dichloromethane.

The resulting mixture was allowed to warm to room temperature and then stirred for an additional two hours. At the end of this time the mixture was diluted with diethyl ether, washed successively with sodium bisulfite solution, sodium bicarbonate solution, and brine solution. The organic layer was separated and dried over anhydrous magnesium sulfate to yield 4,5-dimethoxy-7-oxa-bicyclo[4.1.0]heptane, bp 110° C. at 20 mm Hg.

The proton magnetic resonance spectrum (CDCl$_3$) showed peaks at δ 1.9–2.3 (multiplet, 4 protons), δ 3.15 (broad singlet, 2 protons), δ 3.3–3.5 (multiplet, 8 protons).

Step 4

Preparation of 4,5-dimethoxy-2-(1-pyrrolidinyl)cycohexanol

The oxirane from Step 3 (31.6 mmol) was mixed with 2 mL of water and 10 mL of pyrrolidine and the resulting mixture heated at 85° C. for two hours. The mixture was then concentrated and the residue distilled at 100°–110° C. at 1 mm Hg to yield 4,5-dimethoxy-2-(1-pyrrolidinyl)-cycohexanol.

The proton magnetic resonance spectrum (CDCl$_3$) showed peaks at δ 1.15 (doublet of doublets, 1 proton), δ 1.5–2.1 (multiplet, 7 protons), δ 2.4–2.9 (multiplet, 5 protons), and δ 3.1–3.9 (multiplet, 9 protons).

Step 5

Preparation of N-[4,5-dimethoxy-2-(1-pyrrolidinyl)cyclohexyl]-N-methylbenzenemethanamine The cyclohexanol from Step 4 (8.7 mmol) was dissolved in 20 mL of dichloromethane together with 10 mmol of triethylamine and the resulting mixture was cooled to 0° C. and treated with 9.5 mmol of methanesulfonyl chloride. This mixture was stirred at 0° C. for two hours and then allowed to warm to room temperature. This mixture was diluted with additional dichloromethane and washed twice with water. The organic layer was separated, dried under anhydrous magnesium sulfate, and concentrated under vacuum.

This crude mesylate (3 g) was mixed with 10 mL of N-methyl-N-benzylamine, and 1 mL of water and the resulting mixture was heated at 88° C. on an oil bath for two hours. The mixture was cooled, diluted with dichloromethane, and washed with 1M sodium hydroxide solution. The organic layer was separated, dried over anhydrous magnesium sulfate, and concentrated under vacuum. The residue was distilled to yield N-[4,5-dimethoxy-2-(1-pyrrolidinyl)cyclohexyl]-N-methylbenzenemethanamine, bp 170° C. at 0.4 mm Hg.

The infrared spectrum showed principle absorption peaks at 2932, 1454, and 1110 reciprocal centimeters.

The proton magnetic resonance spectrum (CDCl$_3$) showed peaks at δ 2.4 (doublet of doublets, 1 proton), δ 1.7–2.0 (multiplet, 7 protons), δ 2.1–2.3 (multiplet, 4 protons), δ 2.6–2.8 (multiplet, 4 protons), δ 2.8–3.0 (multiplet, 2 protons), δ 3.1–3.2 (multiplet, 1 proton), δ 3.37–3.38 (singlet, 6 protons), δ 3.68 (broad, 2 protons), and δ 7.1–7.4 (multiplet, 5 protons).

Step 6

Preparation of N-Methyl-4,5-dimethoxy-2-(1-pyrrolidinyl)cyclohexanamine

The N-benzylated amine from Step 5 (2.7 mmol) was dissolved in 30 mL of ethanol and treated with 1 mass equivalent of palladium hydroxide on carbon. This mixture was placed under an atmosphere of hydrogen gas, initially at 50 psi (445 kPa) for 12 hours.

The catalysts was then removed by filtration through Celite ® filter aid and evaporated to a syrup. The product was distilled at 110° C. at 0.5 mm Hg.

The infrared spectrum showed principal absorption peaks at 3308, 2949, 1441, and 1108 reciprocal centimeters.

The proton magnetic resonance spectrum (CDCl$_3$) showed peaks at δ 0.98 (doublet, 1 proton), δ 1.67–1.96

(multiplet, 7 protons), δ 2.40 (singlet, 3 protons), δ 2.41-2.7 (multiplet 7 protons), δ 3.18-3.24 (multiplet, 1 proton), δ 3.38 (singlet, 3 protons), δ 3.42 (singlet, 3 protons), and δ 3.72 (broad singlet, 1 proton).

Step 7
Preparation of N-[4,5-dimethoxy-2-(1-pyrrolidinyl)cyclohexyl]-2-(3-fluorophenoxy)-N-methylacetamide 3-Fluorophenoxyacetic acid (1.2 mmol) was dissolved in 5 mL of thionyl chloride. The solution was heated under reflux in an oil bath for one hour. At the end of this time, the excess thionyl chloride was removed to yield a sticky oil. This material was dissolved in carbon tetrachloride and the remaining thionyl chloride removed by azeotropic distillation under vacuum.

The diamine from Step 6 (1 mmol) was dissolved in 5 mL of dichloromethane and cooled with an ice bath. The crude acid chloride was dissolved in 5 mL of cold dichloromethane, and the resulting solution was slowly added to the solution of diamine. The solid which separated was collected by filtration and purified by high pressure liquid chromatography over silica gel, eluting with dichloromethane/methanol.

The title compound was obtained, mp 119°-121° C.

The proton magnetic resonance spectrum (CDCl$_3$) showed peaks at δ 1.8 (multiplet) δ 2.98 (singlet, 3 protons), δ 3.28 (singlet), δ 3.31 (singlet, 6 protons), δ 4.88 (doublet, 1 proton), δ 5.12 (doublet, 1 proton), and δ 7.20 (multiplet, 4 protons).

Using the methods detailed in Example 1 above, the following additional compounds were prepared.

TABLE 3

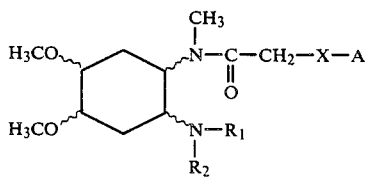

| Example | R$_1$ R$_2$ | X | A | Mp (°C.) |
|---|---|---|---|---|
| 2 | Pyrrolidinyl | Bond | 4-Benzo[b]furanyl | 201-205 |
| 3 | Pyrrolidinyl | Bond | 4-Benzo[b]thiophenyl | 219-220 |
| 4 | Pyrrolidinyl | —O— | 4-Chloro-3,5-dimethylphenyl | 164-166 |
| 5 | Pyrrolidinyl | —O— | 3,4-Dichlorophenyl | 195-200 |
| 6 | Pyrrolidinyl | Bond | 1-Naphthalenyl | 198-201 |
| 7 | Pyrrolidinyl | Bond | 3,4-Dichlorophenyl | 145-148 |
| 8 | Pyrrolidinyl | Bond | 9-Fluorenyl | 245 (dec) |
| 9 | Pyrrolidinyl | —O— | 2,4-Dichloro-3,5-dimethylphenyl | 155-158 |

We claim:
1. A compound having structural Formula I

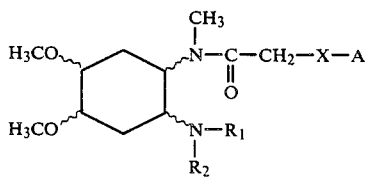 I wherein the methoxy groups attached to the cyclohexane moiety are cis to one another and the two nitrogen atoms attached to the cyclohexane moiety are trans to one another;

X is a direct bond, or is —O— or —S—;

R$_1$ and R$_2$, together with the nitrogen atom to which they are attached form a pyrrolidinyl ring A is selected from

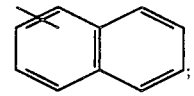

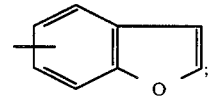

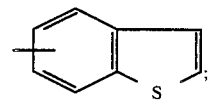

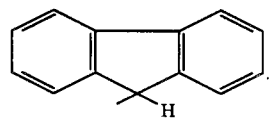

phenyl;

phenyl substituted with from one to four halogen atoms;

phenyl substituted with one or two alkyl groups of from one to four carbon atoms;

phenyl substituted with one or two alkoxy groups of from one to four carbon atoms; or phenyl substituted with one or two alkyl groups of from one to four carbon atoms and one or two halogen atoms; or a pharmaceutically acceptable acid addition salt thereof.

2. A compound as defined by claim 1 wherein X is a direct bond.

3. A compound as defined by claim 1 where X is an oxygen atom.

4. A compound as defined by claim 1 wherein X is a sulfur atom.

5. A compound as defined by claim 2 selected from [1R-(1α,2β,4β,5β)]-N-[4,5-dimethoxy-2-(1-pyrrolidinyl)cyclohexyl]-N-methyl-4-benzofuranacetamide;

[1S-(1α,2β,4β,5β)]-N-[4,5-dimethoxy-2-(1-pyrrolidinyl)cyclohexyl]-N-methyl-4-benzofuranacetamide;

[1R-(1α,2β,4α,5α)]-N-[4,5-dimethoxy-2-(1-pyrrolidinyl)cyclohexyl]-N-methyl-4-benzofuranacetamide;

[1S-(1α,2β,4α,5α)]-N-[4,5-dimethoxy-2-(1-pyrrolidinyl)cyclohexyl]-N-methyl-4-benzofuranacetamide;

or a pharmaceutically acceptable acid addition salt thereof.

6. A compound as defined by claim 2 selected from [1R-(1α,2β,4β,5β)]-N-[4,5-dimethoxy-2-(1-pyrrolidinyl)cyclohexyl]-N-methylbenzo[b]thiophene-4-acetamide;

[1S-(1α,2β,4β,5β)]-N-[4,5-dimethoxy-2-(1-pyrrolidinyl)cyclohexyl]-N-methylbenzo[b]thiophene-4-acetamide;

[1R-(1α,2β,4α,5α)]-N-[4,5-dimethoxy-2-(1-pyrrolidinyl)cyclohexyl]-N-methylbenzo[b]thiophene-4-acetamide;

[1S-(1α,2β,4α,5α)]-N-[4,5-dimetohxy-2-(1-pyrrolidinyl)cyclohexyl]-N-methylbenzo[b]thiophene-4-acetamide;

or a pharmaceutically acceptable acid addition salt thereof.

7. A compound as defined by claim 2 selected from

[1R-(1α,2β,4β,5β)]-2-(4-chloro-3,5-dimethylphenoxy)-N-[4,5-dimethoxy-2-(1-pyrrolidinyl)cyclohexyl]-N-methylacetamide;

[1S-(1α,2β,4β,5β)]-2-(4-chloro-3,5-dimethylphenoxy)-N-[4,5-dimethoxy-2-(1-pyrrolidinyl)cyclohexyl]-N-methylacetamide;

[1R-(1α,2β,4α,5α)]-2-(4-chloro-3,5-dimethylphenoxy)-N-[4,5-dimethoxy-2-(1-pyrrolidinyl)cyclohexyl]-N-methylacetamide;

[1S-(1α,2β,4α,5α)]-2-(4-chloro-3,5-dimethylphenoxy)-N-[4,5-dimethoxy-2-(1-pyrrolidinyl)cyclohexyl]-N-methylacetamide;

or a pharmaceutically acceptable acid addition salt thereof.

8. A compound as defined by claim 2 selected from

[1R-(1α,2β,4β,5β)]-N-[4,5-dimethoxy-2-(1-pyrrolidinyl)cyclohexyl]-N-methyl-1-naphthaleneacetamide;

[1S-(1α,2β,4β,5β)]-N-[4,5-dimethoxy-2-(1-pyrrolidinyl)cyclohexyl]-N-methyl-1-naphthaleneacetamide;

[1R-(1α,2β,4α,5α)]-N-[4,5-dimethoxy-2-(1-pyrrolidinyl)cyclohexyl]-N-methyl-1-naphthaleneacetamide;

[1S-(1α,2β, 4α,5α)]-N-[4,5-dimethoxy-2-(1-pyrrolidinyl)cyclohexyl]-N-methyl-1-naphthaleneacetamide;

or a pharmaceutically acceptable acid addition salt thereof.

9. A compound as defined by claim 2 selected from

[1R-(1α,2β,4β,5β)]-3,4-dichloro-N-[4,5-dimethoxy-2-(1-pyrrolidinyl)cyclohexyl]-N-methylbenzeneacetamide;

[1S-(1α,2β,4β,5β)]-3,4-dichloro-N-[4,5-dimethoxy-2-(1-pyrrolidinyl)cyclohexyl]-N-methylbenzeneacetamide;

[1R-(1α,2β,4α,5α)]-3,4-dichloro-N-[4,5-dimethoxy-2-(1-pyrrolidinyl)cyclohexyl]-N-methylbenzeneacetamide;

[1S-(1α,2β,4α,5α)]-3,4-dichloro-N-[4,5-dimethoxy-2-(1-pyrrolidinyl)cyclohexyl]-N-methylbenzeneacetamide;

or a pharmaceutically acceptable acid addition salt thereof.

10. A compound as defined by claim 2 selected from

[1R-(1α,2β,4β,5β)]-N-[4,5-dimethoxy-2-(1-pyrrolidinyl)cyclohexyl]-N-methyl-9H-fluorene-9-carboxamide;

[1S-(1α,2β,4β,5β)]-N-[4,5-dimethoxy-2-(1-pyrrolidinyl)cyclohexyl]-N-methyl-9H-fluorene-9-carboxamide;

[1R-(1α,2β,4α,5α)]-N-[4,5-dimethoxy-2-(1-pyrrolidinyl)cyclohexyl]-N-methyl-9H-fluorene-9-carboxamide;

[1S-(1α,2β,4α,5α)]-N-[4,5-dimethoxy-2-(1-pyrrolidinyl)cyclohexyl]-N-methyl-9H-fluorene-9-carboxamide;

or a pharmaceutically acceptable acid addition salt thereof.

11. A compound as defined by claim 3 selected from

[1R-(1α,2β,4β,5β)]-2-(3,4-dichlorophenoxy)-N-[4,5-dimethoxy-2-(1-pyrrolidinyl)cyclohexyl]-N-methylacetamide;

[1S-(1α,2β,4β,5β)]-2-(3,4-dichlorophenoxy)-N-[4,5-dimethoxy-2-(1-pyrrolidinyl)cyclohexyl]-N-methylacetamide;

[1R-(1α,2β,4α,5α)]-2-(3,4-dichlorophenoxy)-N-[4,5-dimethoxy-2-(1-pyrrolidinyl)cyclohexyl]-N-methylacetamide;

[1S-(1α,2β,4α,5α)]-2-(3,4-dichlorophenoxy)-N-[4,5-dimethoxy-2-(1-pyrrolidinyl)cyclohexyl]-N-methylacetamide;

or a pharmaceutically acceptable acid addition salt thereof.

12. A compound as defined by claim 3 selected from

[1R-(1α,2β,4β,5β)]-N-[4,5-dimethoxy-2-(1-pyrrolidinyl)cyclohexyl]-2-(3-fluorophenoxy)-N-methylacetamide;

[1S-(1α,2β,4β,5β)]-N-[4,5-dimethoxy-2-(1-pyrrolidinyl0cyclohexyl]-2-(3-fluorophenoxy)-N-methylacetamide;

[1R-(1α,2β,4α,5α)]-N-[4,5-dimethoxy-2-(1-pyrrolidinyl)cyclohexyl]-2-(3-fluorophenoxy)-N-methylacetamide;

[1S-(1α,2β,4α,5α)]-N-[4,5-dimethoxy-21 -(1-pyrrolidinyl)cyclohexyl]-2-(3-fluoropheonxy)-N-methylacetamide;

or a pharmaceuitcally acceptable acid addition salt thereof.

13. A compound as defined by claim 3 selected from

[1R-(1α,2β,4β,5β)]-2-(2,4-dichloro-3,5-dimethylphenoxy)-N-[4,5-dimetohxy-2-(1-pyrrolidinyl)cyclohexyl]-N-methylacetamide;

[1S-(1α,2β,4β,5β)]-2-(2,4-dichloro-3,4-dimethylphenoxy)-N-[4,5-dimethoxy-2-(1-pyrrolidinyl)cyclohexyl]-N-methalacetamide;

[1R-(1α,2β,4α,5α)]-2-(2,4-dichloro-3,5-dimethylphenoxy)-N-[4,5-dimethoxy-2-(1-pyrrolidinyl)cyclohexyl]-N-methylacetamide;

[1S-(1α,2β,4α,5α)]-2-(2,4-dichloro-3,5-dimethylphenoxy)-N-[4,5-dimethoxy-2-(1-pyrrolidinyl)cyclohexyl]-N-methylacetamide;

or a pharmaceutically acceptable acid addition salt thereof.

14. A compound as defined by claim 3 selected from

[1R-(1α,2β,4β,5β)]-N-[4,5-dimethoxy-2-(1-pyrrolidinyl)cyclohexyl]-N-methyl-2-(2,3,4,5-tetrachlorophenoxy)acetamide;

[1S-(1α,2β,4β,5β)]-N-[4,5-dimethoxy-2-(1-pyrrolidinyl)cyclohexyl]-N-methyl-2-(2,3,4,5-tetrachlorophenoxy)acetamide;

[1R-(1α,2β,4α,5α)]-N-[4,5-dimethoxy-2-(1-pyrrolidinyl)cyclohexyl]-N-methyl-2-(2,3,4,5-tetrachlorophenoyx)acetamide;

[1S-(1α, 2β,4α,5α)]-N-[4,5-dimethoxy-2-(1-pyrrolidinyl)cyclohexyl]-N-methyl-2-(2,3,4,5-tetrachlorophenoxy)acetamide;

or a pharmaceutically acceptable acid addition salt thereof.

15. A pharmaceutical composition useful for treating pain in a mammal comprising an analgesically effective amount of a compound as defined by claim 1 in combination with a pharmaceutically acceptable carrier.

16. A method for treating pain in mammal comprising administering to a mammal in need of such treatment an analgesically effective amount of a compound as defined by claim 1.

* * * * *